(12) United States Patent
Piron et al.

(10) Patent No.: US 10,925,676 B2
(45) Date of Patent: Feb. 23, 2021

(54) METHOD, SYSTEM AND APPARATUS FOR CONTROLLING A SURGICAL NAVIGATION SYSTEM

(71) Applicant: SYNAPTIVE MEDICAL INC., Toronto (CA)

(72) Inventors: Cameron Anthony Piron, Toronto (CA); Michael Frank Gunter Wood, Toronto (CA); Gal Sela, Toronto (CA); Joshua Lee Richmond, Toronto (CA); Murugathas Yuwaraj, Toronto (CA); Stephen B. E. McFadyen, Toronto (CA); Kelly Noel Dyer, Toronto (CA); Monroe M. Thomas, Toronto (CA); Wes Hodges, Toronto (CA); Simon Alexander, Toronto (CA); David Gallop, Toronto (CA)

(73) Assignee: SYNAPTIVE MEDICAL INC., Toronto (CA)

(*) Notice: Subject to any disclaimer, the term of this patent is extended or adjusted under 35 U.S.C. 154(b) by 547 days.

(21) Appl. No.: 15/694,241

(22) Filed: Sep. 1, 2017

(65) Prior Publication Data
US 2018/0014892 A1 Jan. 18, 2018

Related U.S. Application Data

(63) Continuation of application No. 14/775,192, filed as application No. PCT/CA2014/000247 on Mar. 14, 2014, now abandoned.
(Continued)

(51) Int. Cl.
*A61B 5/00* (2006.01)
*A61B 34/20* (2016.01)
(Continued)

(52) U.S. Cl.
CPC .............. *A61B 34/20* (2016.02); *A61B 34/25* (2016.02); *A61B 90/90* (2016.02); *A61B 90/98* (2016.02);
(Continued)

(58) Field of Classification Search
CPC ......... A61B 34/20; A61B 34/25; A61B 90/98; A61B 90/90; A61B 2090/103;
(Continued)

(56) References Cited

U.S. PATENT DOCUMENTS 7,123,149 B2   10/2006   Nowak et al.
7,643,862 B2 *  1/2010   Schoenefeld .......... A61B 34/20
                                                    600/407

(Continued)

FOREIGN PATENT DOCUMENTS

WO    2011123669 A1    10/2011

OTHER PUBLICATIONS

Fischer et al. Utilizing Image Guided Surgery for User Interaction in Medical Augmented Reality; www.gris.uni-tuebingen.de/publics/paper/Fischer-2005-Utilizing.pdf.
(Continued)

*Primary Examiner* — Joel Lamprecht
(74) *Attorney, Agent, or Firm* — Perry + Currier

(57) ABSTRACT

A method, system and apparatus for controlling a surgical navigation system are provided. The method 1 comprises receiving image data at a processor from a tracking system; receiving, at a processor, an identifier of a surgical instrument within a field of view of the tracking system; generating, at the processor, output data based on the identifier of the surgical instrument; and transmitting the output data to at least one output device connected to the processor, for controlling the output device.

19 Claims, 15 Drawing Sheets

Related U.S. Application Data

(60) Provisional application No. 61/801,530, filed on Mar. 15, 2013, provisional application No. 61/800,155, filed on Mar. 15, 2013, provisional application No. 61/818,280, filed on May 1, 2013, provisional application No. 61/924,993, filed on Jan. 8, 2014.

(51) Int. Cl.
| | | |
|---|---|---|
| *A61B 90/90* | (2016.01) | |
| *A61B 90/98* | (2016.01) | |
| *A61B 34/00* | (2016.01) | |
| *A61B 17/00* | (2006.01) | |
| *A61B 90/50* | (2016.01) | |
| *A61B 34/30* | (2016.01) | |
| *A61B 90/00* | (2016.01) | |
| *A61B 34/10* | (2016.01) | |
| *A61B 90/10* | (2016.01) | |

(52) U.S. Cl.
CPC .............. *A61B 34/30* (2016.02); *A61B 90/50* (2016.02); *A61B 2017/00207* (2013.01); *A61B 2034/105* (2016.02); *A61B 2034/2046* (2016.02); *A61B 2034/2055* (2016.02); *A61B 2034/2059* (2016.02); *A61B 2034/2065* (2016.02); *A61B 2034/2072* (2016.02); *A61B 2034/2074* (2016.02); *A61B 2034/256* (2016.02); *A61B 2090/103* (2016.02); *A61B 2090/364* (2016.02); *A61B 2560/0475* (2013.01)

(58) Field of Classification Search
CPC ........ A61B 2034/105; A61B 2090/364; A61B 2034/2065; A61B 2034/2074; A61B 2034/2072; A61B 2034/2059; A61B 2034/2046; A61B 34/30; A61B 90/50; A61B 2560/0475; A61B 2034/256; A61B 2034/2055; A61B 2017/00207
See application file for complete search history.

(56) References Cited

U.S. PATENT DOCUMENTS

| | | | |
|---|---|---|---|
| 2004/0106916 A1 | 6/2004 | Quaid et al. | |
| 2006/0142656 A1 | 6/2006 | Malackowski et al. | |
| 2007/0016008 A1* | 1/2007 | Schoenefeld | A61B 90/36 600/424 |
| 2007/0078340 A1* | 4/2007 | Wilcox | G01S 15/8906 600/437 |
| 2008/0200926 A1* | 8/2008 | Verard | A61B 5/06 606/130 |
| 2009/0036902 A1 | 2/2009 | DiMaio et al. | |
| 2010/0210938 A1 | 8/2010 | Verard et al. | |
| 2016/0038253 A1* | 2/2016 | Piron | A61B 90/90 600/424 |

OTHER PUBLICATIONS

Image Guided Surgical Interventions. Curr Probl Surg, Sep. 2009 pp. 730-766.

Kaur, Gulsheen et al.—CASMIL: A comprenhensive software/toolkit for image-guided neurosurgeries; the International Journal of Medical Robotics and Computor Assisted Surgery 2006; 2: 123-138.

Kocev, Bojan et al.—An approach for Projector-based Surgeon-Computer Interaction using Tracked Instruments; Informatik 2011.

Lindseth, Frank: Ultrasound Guided Surgery: Multimodal Visulation and Navigation Accuracy; Norwegian University of Science and Technology, Dec. 2002.

* cited by examiner

METHOD, SYSTEM AND APPARATUS FOR CONTROLLING A SURGICAL NAVIGATION SYSTEM

CROSS REFERENCE TO RELATED APPLICATION

This application is a continuation of U.S. patent application Ser. No. 14/775,192, filed Sep. 11, 2015, which claims priority from U.S. Provisional Application Nos. 61/801,530, filed Mar. 15, 2013; 61/800,155, filed Mar. 15, 2013; 61/818,280, filed May 1, 2013; and 61/924,993, filed Jan. 8, 2014. The contents of all the above-mentioned provisional applications are incorporated herein by reference.

FIELD

The specification relates generally to navigation systems, and specifically to a method, system and apparatus for navigation systems for use in image guided medical procedures.

BACKGROUND

The performance of surgical procedures often calls for a surgeon to access significant volumes of information. As a result, various surgical assistance systems exist that place some of this information at the surgeon's disposal. However, conventional technologies for navigating such systems to access the desired information may require the surgeon to deposit surgical instruments and manipulate other devices, or to attempt to communicate desired system interactions to an assistant. As a result, although all the required information may be present, access to that information during the procedure may be hampered.

SUMMARY

An aspect of the specification provides a method of controlling a surgical navigation system, comprising: receiving, at a processor, an identifier of a surgical instrument within a field of view of a tracking system; generating, at the processor, output data based on the identifier of the surgical instrument; and transmitting the output data to an output device connected to the processor, for controlling the output device. Further aspects of the specification include a computing device configured to perform the above method, and a non-transitory computer-readable medium storing a plurality of computer readable instructions executable by a processor for implementing the above method.

BRIEF DESCRIPTIONS OF THE DRAWINGS

Embodiments are described with reference to the following figures, in which.

DETAILED DESCRIPTION OF THE EMBODIMENTS

Various embodiments and aspects are described below. The following description, and the accompanying drawings, are illustrative and are not to be construed as limiting in scope.

Figure 1:
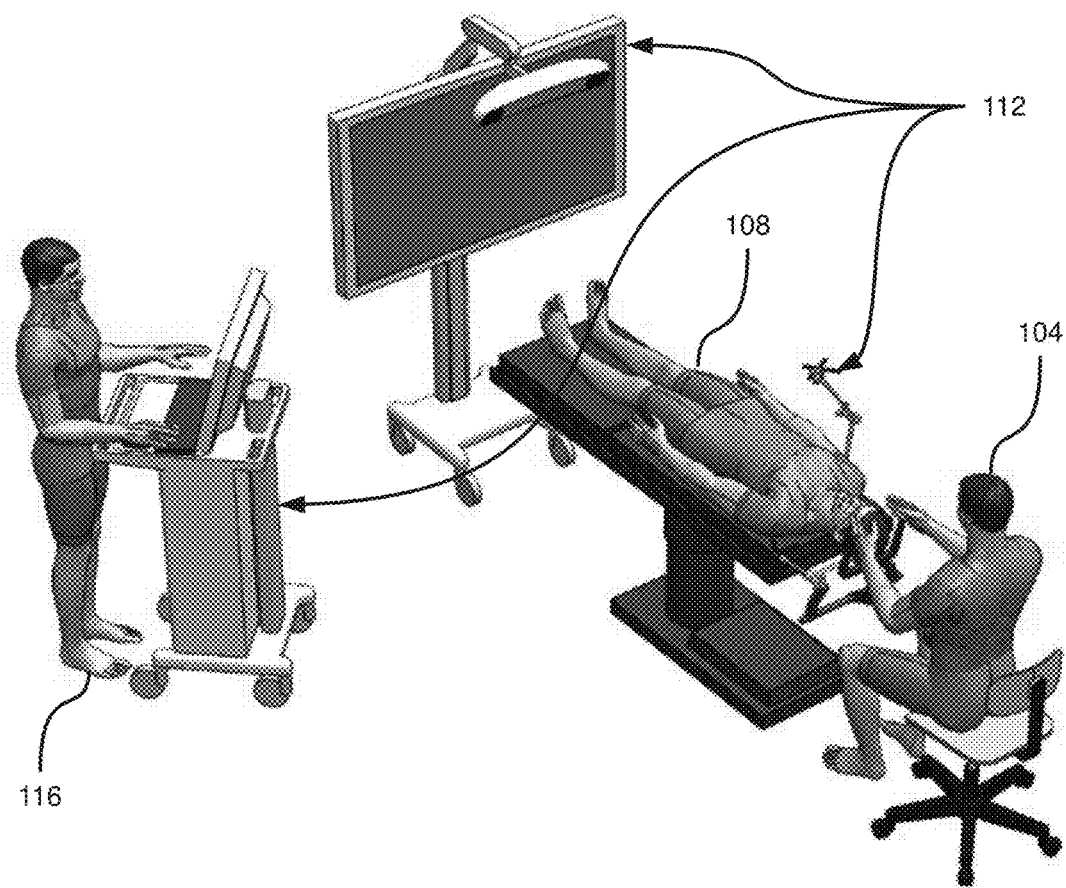
FIG. 1 depicts a navigation system in use in a surgical procedure, according to a non-limiting embodiment.

FIG. 1 depicts a surgeon 104 conducting a minimally invasive port-based surgical procedure on a patient 108 in an operating room (OR) environment. The surgical procedure is supported by a navigation system 112, including a computing device connected to a variety of input devices (e.g. a tracking sensor such as a camera, a keyboard and mouse and the like) and controlling a variety of output devices (e.g. a display, illumination equipment and the like). System 112 also includes a variety of surgical instruments, whose motions may be tracked by system 112. An assistant or operator 116 can also be present, and both surgeon 104 and assistant 116 can operate system 112. In particular, as will be discussed below, system 112 is configured to control the output devices based on input from a variety of sources, including not only the above mentioned input devices, but also the tracked surgical instruments that are manipulated by surgeon 104 during the procedure.

Figure 2:
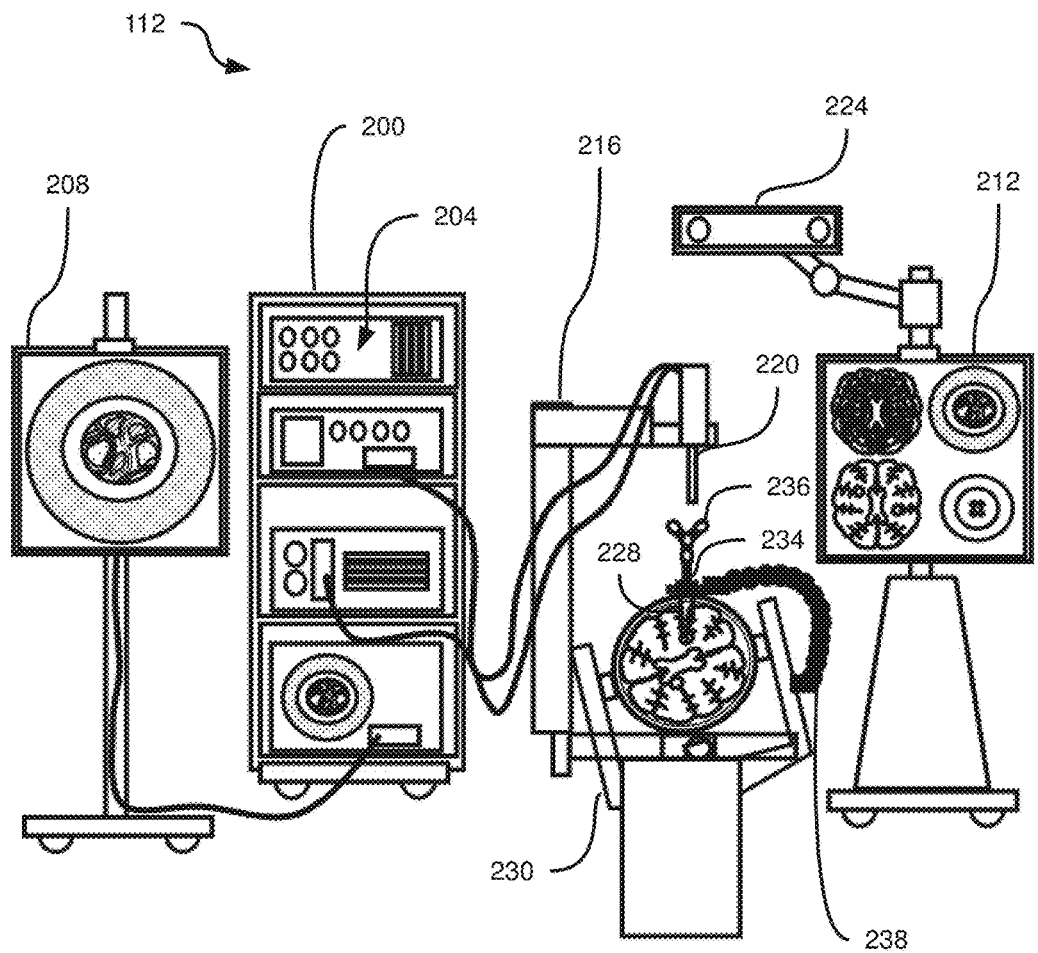
FIG. 2 depicts a schematic diagram of the navigation system of FIG. 1, according to a non-limiting embodiment.

Turning now to FIG. 2, a block diagram illustrating certain components of system 112 is depicted. As seen in FIG. 2, system 112 includes an equipment tower 200 supporting a computing device 204, along with other equipment. Equipment tower 200 is mounted on a rack, cart, or the like, and may also support a power supply for the remaining components of system 112.

Computing device 204 is connected to output devices including a display, such as displays 208 and 212, and a robotic arm 216. Each of displays 208 and 212 can be based on any suitable display technology. For example, display 208 can be a flat panel display comprising any one of, or any suitable combination of, a Liquid Crystal Display (LCD), a plasma display, an Organic Light Emitting Diode (OLED) display, and the like. Other display technologies on which displays 208 and 212 can be based include projection systems, cathode ray tube (CRT) displays, Computing device 204 is also connected to input devices including an optical scope 220 (also referred to as an exoscope), and a tracking sensor such as a tracking camera 224, which can be a stereoscopic camera. Examples of such cameras, such as the "Polaris" unit available from Northern Digital Imaging (NDI), will occur to those skilled in the art. Tracking camera 224 may be configured to receive visible light, IR, or both. Although tracking camera 224 is discussed herein as an example tracking sensor, it is to be understood that other tracking sensors may also be used instead of, or in addition to, tracking camera 224. Thus, any references to tracking camera 224 below may also refer, in other embodiments, to any of a variety of suitable tracking systems known to those skilled in the art.

Minimally invasive brain surgery using access ports is a recently conceived method of performing surgery on brain tumors previously considered inoperable. Such minimally invasive procedures are performed through a relatively small opening in a patient's skull. To that end, system 112 also includes an access port 228 for insertion through the skull of patient 108—which is immobilized by a holder 230—and into the brain of patient 108. An introducer 234 with an atraumatic tip (for reducing damage to brain tissue during the insertion of access port 228) is inserted into access port 228, and access port 228 and introducer 234 together are inserted into the skull of patient 108.

Introducer 234 includes fiduciary markers 236 such as IR-reflecting markers, that are detectable by tracking camera 224. In the present embodiment, tracking camera 224 can emit infrared light, which is reflected by markers 236 and permits tracking camera 224 (which is sensitive to IR radiation) to capture images from which markers 236 can readily be isolated. As will be discussed below, robotic arm 216 and other instrumentation can also carry fiduciary markers. Camera 224 in conjunction with computing device 204 can determine the spatial positions of markers 236 using conventional motion tracking algorithms. Computing device 204 is therefore configured to track the position of markers 236 (and by extension, the position of introducer 228) as introducer 234 is moved within the field of view of tracking camera 224. In addition, it is contemplated that the spatial position of patient 108's skull was previously determined and stored by computing device 204.

Because introducer 234 is held within access port 228 during insertion of access port 228 into the skull of patient 108, markers 236 allow computing device 204 to track not only introducer 234, but also access port 228 itself, even if access port 228 does not carry any markers. The tracked position of introducer 234 relative to the known position of the skull of patient 108 can be presented on one or both of displays 208 and 212. Various views (e.g. axial, sagittal, coronal, perpendicular to tool tip, in-plane of tool shaft, and the like) of the relative positions of introducer 234, access port 228 and the skull can be presented on displays 208 and 212.

Once introducer 234 and access port 228 have been inserted into the brain of patient 108, introducer 234 may be removed from access port 228 to allow access to the brain tissue through a central opening of access port 228. In some embodiments, access port 228 does not carry any fiduciary markers, and therefore may not be able to be directly tracked after the removal of introducer 234. However, other surgical instruments carrying markers can be used to indirectly track access port 228. In other embodiments, including the embodiments discussed in detail below, access port 228 itself can carry fiduciary markers 236.

System 112 can also include an articulated arm 238 anchored at one end to holder 230, and having at an opposite end a clamp for engaging access port 228. Arm 238 may be employed to fix the position of access port 228 after insertion. Arm 238 may also have locked and unlocked positions, such that in the locked position access port 228 is not permitted to move, while in the unlocked position movement (at least in certain axes) by access portion 228 is permitted.

Figure 3:
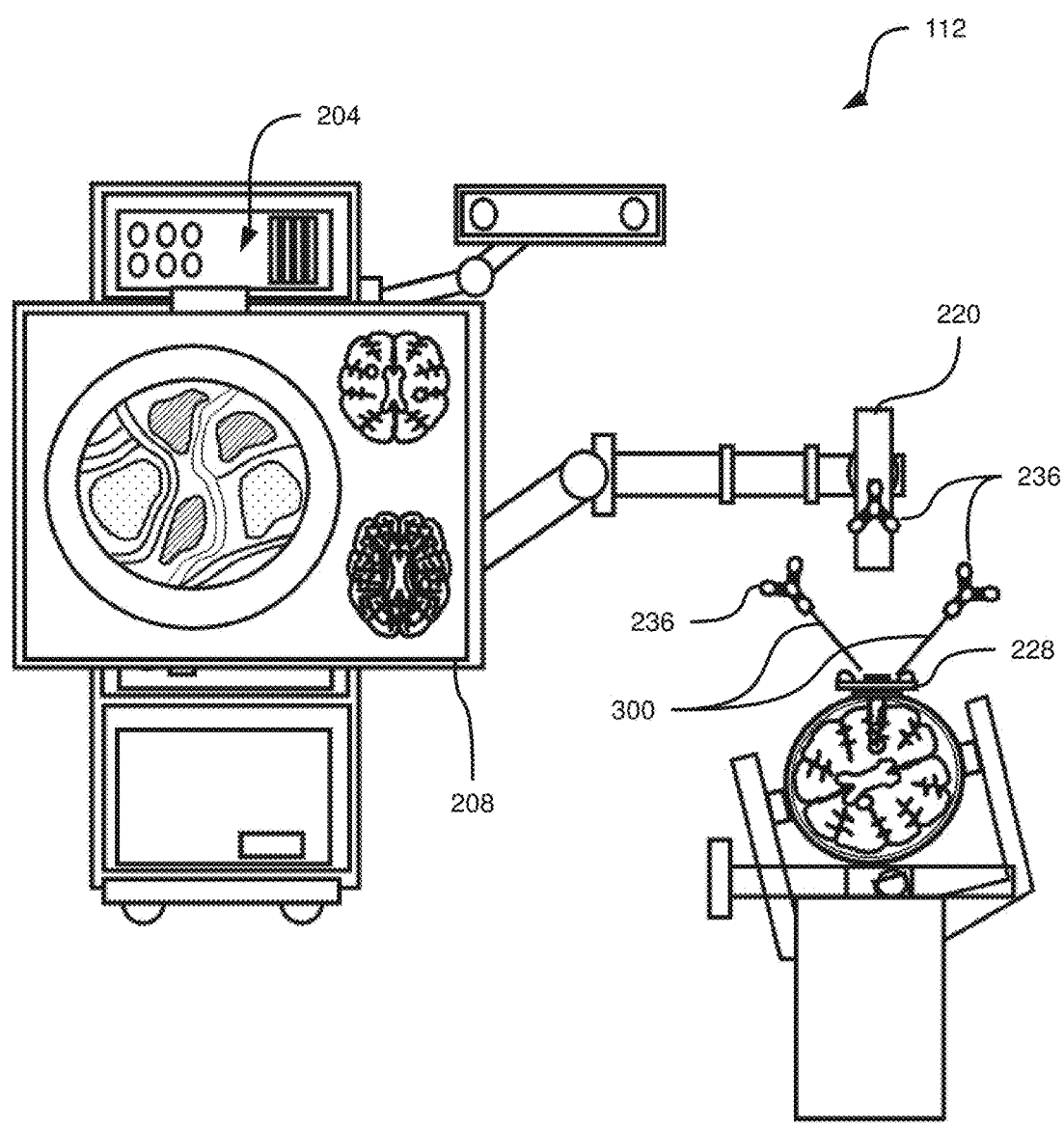
FIG. 3 depicts a schematic diagram of the navigation system of FIG. 1, according to another non-limiting embodiment.

Turning to FIG. 3, another depiction of system 112 is illustrated, in which only display 208 is included. Additional surgical instruments 300 are also shown (such as a probing instrument and a suction instrument, for example), each carrying fiduciary markers 236. Further, as mentioned above, scope 220 also carries markers 236 in FIG. 3.

In general, therefore, the movements of certain components of system 112, particularly surgical instruments, can be tracked in space. As will be discussed below in greater detail, computing device 204 can control the output devices of system 112 based on those tracked movements. The control of output devices need not be based only on tracked movements—output control can also be based on other contextual data, including the specific identity of the tracked instruments, as well as surgical planning data. The surgical planning data can include an identifier of the current phase or stage of the surgical procedure, which can be determined at computing device 204 either via receipt of an input from an operator (e.g. surgeon 104), or by other triggers automatically detected by computing device 204. Those triggers can include detection of a tip of access port 228 traversing the outer boundary of the skull, indicating that cannulation is occurring. For example, as will be discussed below, displays 208 and 212 can be controlled to present various selectable interface elements (including menus) based on instrument identities and movements. The components and operation of computing device 204 will now be discussed in greater detail.

Figure 4:
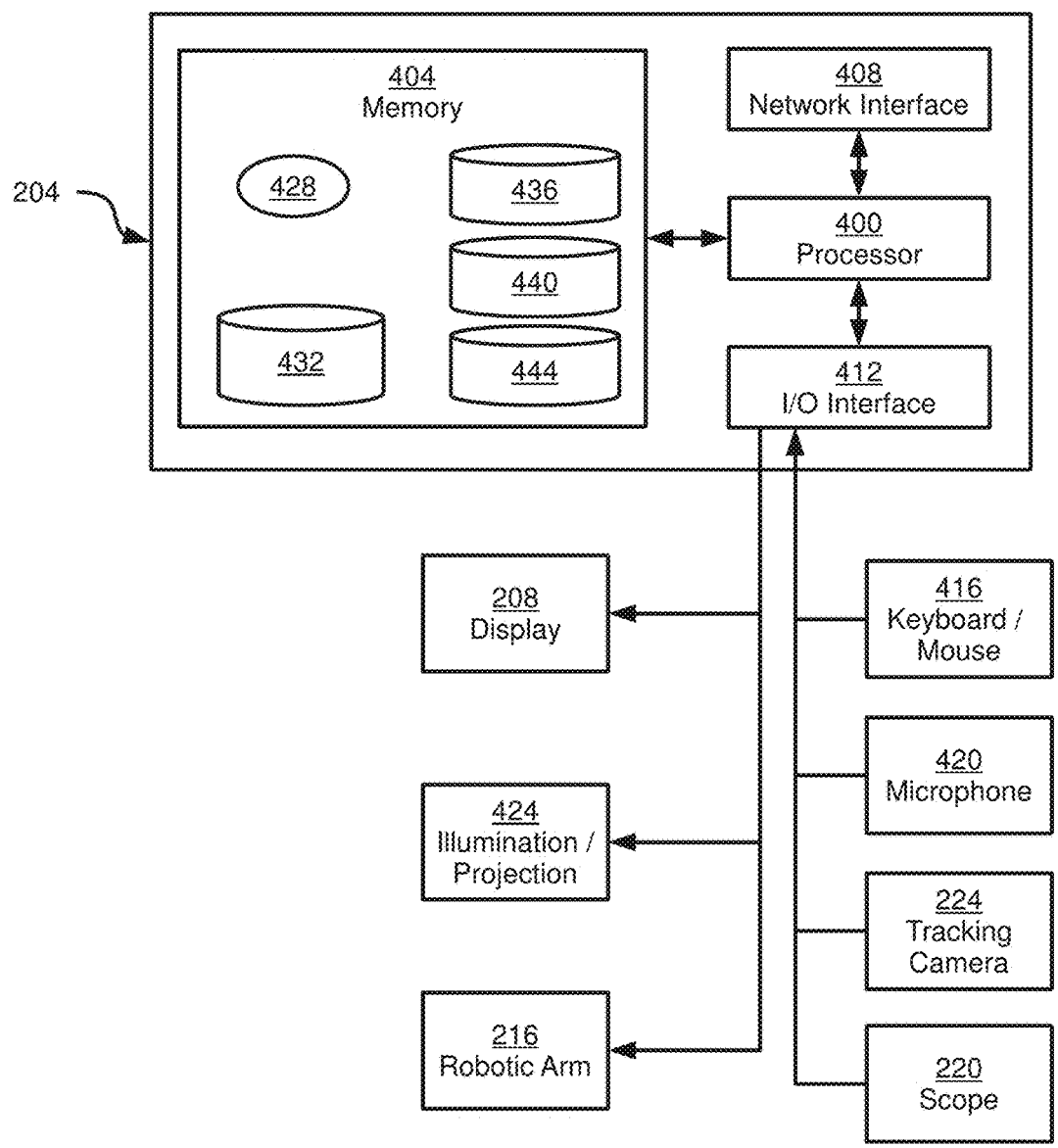
FIG. 4 depicts a computing device of the system of FIG. 1, according to a non-limiting embodiment.

Turning to FIG. 4, a schematic diagram of certain components of computing device 204 is shown in relation to other components of system 112. Computing device 204 includes a central processing unit (also referred to as a microprocessor or simply a processor) 400 interconnected with a non-transitory computer readable storage medium such as a memory 404. Processor 400 and memory 404 are generally comprised of one or more integrated circuits (ICs), and can have a variety of structures, as will now occur to those skilled in the art (for example, more than one CPU can be provided).

Memory 404 can be any suitable combination of volatile (e.g. Random Access Memory ("RAM")) and non-volatile (e.g. read only memory ("ROM"), Electrically Erasable Programmable Read Only Memory ("EEPROM"), flash memory, magnetic computer storage device, or optical disc) memory. In the present example, memory 404 includes both a volatile memory and a non-volatile memory. Other types of non-transitory computer readable storage medium are also contemplated, such as compact discs (CD-ROM, CD-RW) and digital video discs (DVD).

Computing device 204 also includes a network interface 408 interconnected with processor 400. Network interface 408 allows computing device 204 to communicate with other computing devices via a network (e.g. a local area network (LAN), a wide area network (WAN) or any suitable combination thereof). Network interface 408 thus includes any necessary hardware for communicating over such networks.

Computing device 204 also includes an input/output interface 412, including the necessary hardware for interconnecting processor 400 with various input and output devices. Interface 412 can include, among other components, a Universal Serial Bus (USB) port, an audio port for sending and receiving audio data, a Video Graphics Array (VGA), Digital Visual Interface (DVI) or other port for sending and receiving display data, and any other suitable components.

Via interface 412, computing device 204 is connected to input devices including a keyboard and mouse 416, a microphone 420, as well as scope 220 and tracking camera 224, mentioned above. Also via interface 412, computing device 204 is connected to output devices including illumination or projection components (e.g. lights, projectors and the like), as well as display 208 and robotic arm 216 mentioned above. Other input (e.g. touch screens) and output devices (e.g. speakers) will also occur to those skilled in the art.

Computing device 204 stores, in memory 404, an interface management application 428 (also referred to herein as application 428) comprising a plurality of computer readable instructions executable by processor 400. When processor 404 executes the instructions of application 428 (or, indeed, any other application stored in memory 404), processor 404 performs various functions implemented by those instructions, as will be discussed below. Processor 400, or computing device 204 more generally, is therefore said to be "configured" to perform those functions via the execution of application 428.

Also stored in memory 404 are various data repositories, including patient data 432, surgical instrument definitions 436, input gesture definitions 440, and output control rules 444. Patient data 432 includes a surgical plan defining the various steps of the minimally invasive surgical procedure, as well as image data relating to patient 108, such as Magnetic Resonance Imaging (MRI) and Computed Tomography (CT) scans, three-dimensional models of the brain of patient 108 and the like. Instrument definitions 436 includes data defining characteristics of at least one of the surgical instruments to be used in the surgical procedure—such characteristics allow computing device 204 to differentiate between instruments in image data received from tracking camera 224. Gesture definitions 440 include data defining various movements of the instruments defined in instrument definitions 436. Finally, rules 444 contain associations between the gestures defined in gesture definitions 440 and output operations to be effected by computing device 204. These repositories will be described in further detail below.

It is to be understood that although repositories 432, 436, 440 and 444 are shown as databases in FIG. 4, their data structures are not particularly limited—the data contained within each repository can be stored in any suitable structure.

Figure 5:
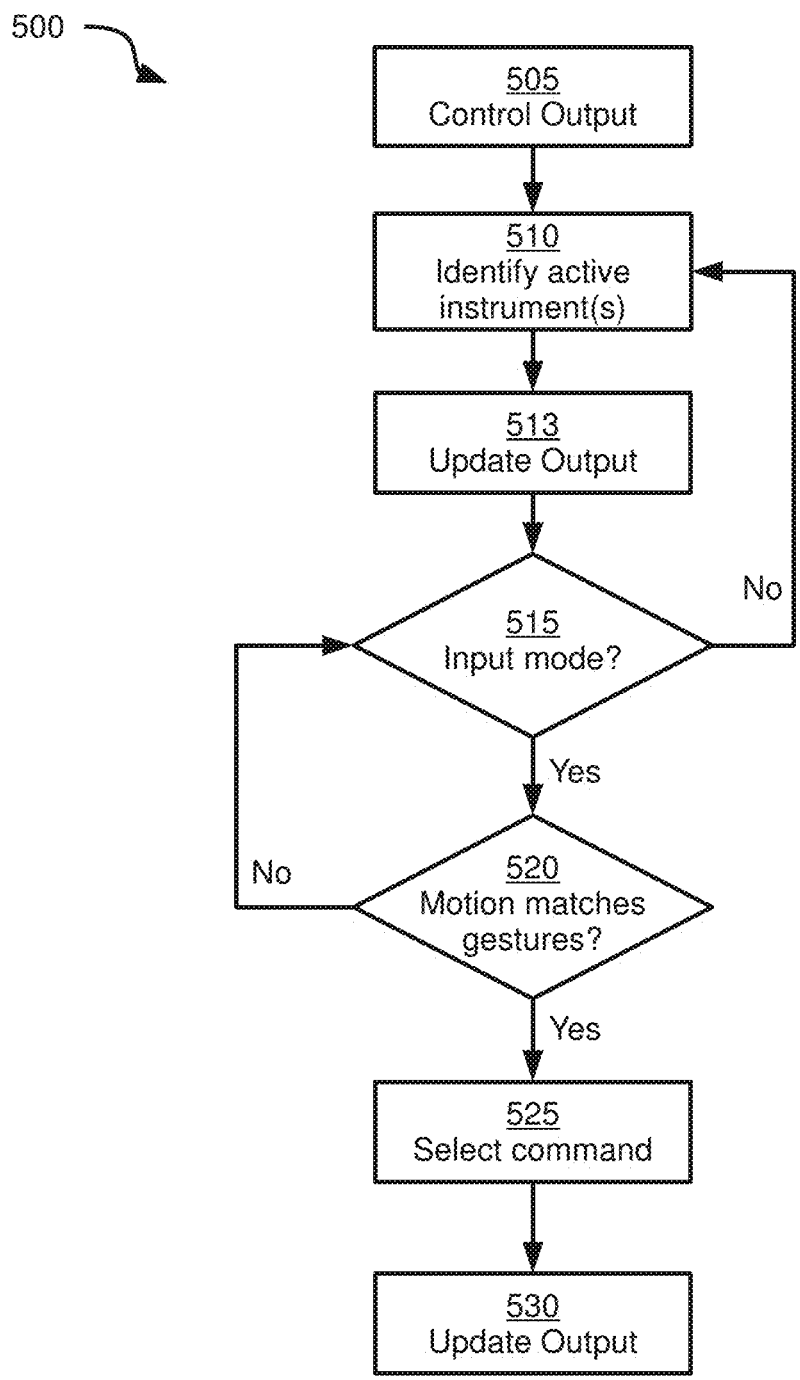
FIG. 5 depicts a method of controlling a surgical navigation system, according to a non-limiting embodiment.

Turning now to FIG. 5, a method 500 of controlling a navigation system, such as system 112, is shown. Method 500 will be described in conjunction with its performance on system 112, and particularly on computing device 204, although it is contemplated that method 500, and variants thereof, can also be adapted to other systems.

Figure 6:
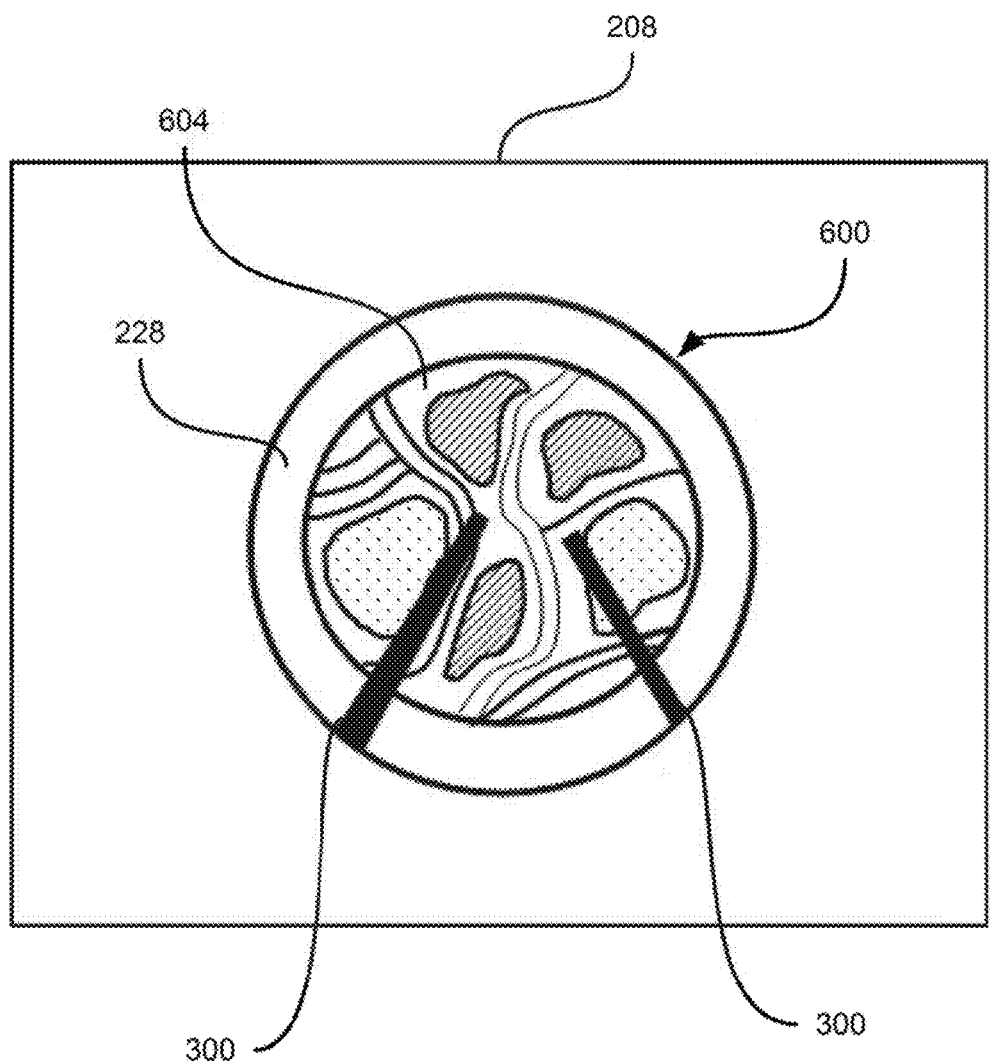
FIG. 6 depicts an example performance of block 505 of the method of FIG. 5, according to a non-limiting embodiment.

At block 505, computing device 204 is configured to control one or more output devices of system 112. To control the output devices of system 112, processor 400 is configured to generate output data and transmit the output data, via I/O interface 412, to the relevant output devices. The nature of the control at block 505—which output devices are controlled and what output data is generated—is not particularly limited. In the present example performance of method 500, at block 505 processor 400 is configured to control display 208 to present a video feed received from scope 220 on display 208. An example of such a feed is shown in FIG. 6, where an image 600 representing a frame of the video feed is presented on display 208. In image 600, a portion of access port 228 is visible, and brain tissue 604 is visible through access port 228. Access port 228 and brain tissue 604 may be visible on display 208 at a configurable magnification greater than 1. Also visible in image 600 are the tips of two surgical instruments 300.

It is also contemplated that at block 505, an overhead light or projector 424 is controlled by computing device 204 to project white light at a predefined brightness onto access port 228 to illuminate brain tissue 604. As will be discussed below, a wide variety of control mechanisms are contemplated, and they need not include overhead lighting in some embodiments. For example, overhead lights may not be controlled by computing device 204 in some embodiments.

Proceeding to block 510, computing device 204 is configured to identify surgical instruments that are active (that is, present in the field of view of tracking camera 224). Computing device 204 receives image data from tracking camera 224 via interface 412. The received image data contains artifacts representing reflected light from markers 236, and computing device 204 is configured to compare the image data, including such artifacts, to instrument definitions 436 to determine which surgical instruments, if any, are present within the field of view of tracking camera 224.

Figure 7:
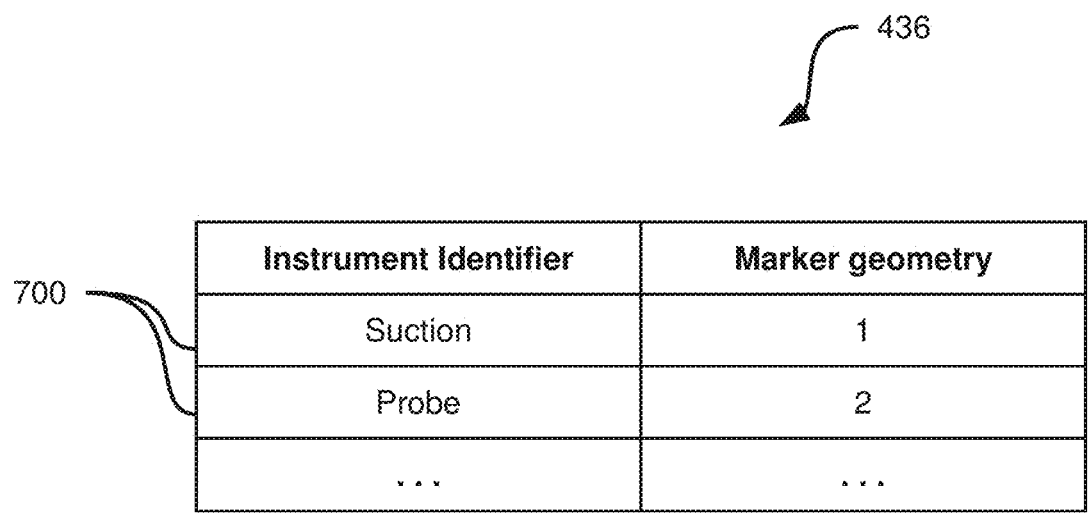
FIG. 7 depicts instrument definitions stored by the computing device of FIG. 4, according to a non-limiting embodiment.

Turning briefly to FIG. 7, an example of instrument definitions 436 is shown. Instrument definitions 436 includes a plurality of records 700, each including an instrument identifier (e.g. "suction") and one or more instrument characteristics. In the present example, each record 700 includes an indication of the geometry of markers 236 attached to that particular instrument (that is, the positions of markers 236 relative to each other). Thus, at block 510, computing device 204 is configured to compare the geometry of markers in image data received from tracking camera 224 to the geometries specified in definitions 436. When the geometry of one or more markers in the image data matches the geometry specified in a given record 700, the corresponding instrument identifier in that record 700 is selected for further processing.

A wide variety of instrument characteristics can be included in records 700 instead of, or in addition to, marker geometry. Other examples of instrument characteristics include marker reflectivity, marker size, and the like. In still other embodiments, surgical instruments can be equipped with RFID tags or other near-field communication devices that broadcast instrument identities to computing device 204.

In some embodiments, tool definitions 436 can be omitted entirely from computing device 204. Instead, tracking camera 224 (or, as mentioned earlier, any other suitable tracking system) can be configured to identify instruments and transmit instrument identifiers and position data to computing device 204, instead of transmitting image data for computing device 204 to process.

Having identified active instruments at block 510, computing device 204 can be configured to perform block 513. At block 513, computing device 204 is configured to generate updated output data for controlling the output devices of system 112 based on the identities of the active instruments. For example, instrument definitions 436 can include output commands in addition to the instrument identifiers and characteristics. Such output commands can cause computing device 204 to select a particular menu of selectable interface elements for presentation on display 208, among a plurality of selectable interface elements contained in application 428. Such output commands can also configure computing device 204 to control illumination and projection equipment 424 in a predefined manner, or to control display 208 to overlay data from repository 432 on image 600 (for example, a three dimensional model of the patient's brain, a CT scan, or the like).

The above-mentioned output commands need not be specified in instrument definitions 436, Instead, such output commands can be specified in planning data in repository 432. For example, each stage of the surgical procedure can contain data identifying the instruments expected to be used for that stage, and specifying output commands for controlling the output devices of system 112. The identification of instruments matching those in a certain stage of the planning data (or matching certain relative states, such as instrument positions, e.g. probe tip within the skull boundary) can indicate that the procedure has reached that certain stage, and computing device 204 can be configured to implement the output commands associated with the stage.

In other embodiments, the performance of block 513 can be omitted. The performance of method 500 therefore proceeds from either of blocks 510 or 513 to block 515.

At block 515, computing device 204 is configured to determine whether an input mode has been activated. In an input mode, the movements of the instruments identified at block 510 can control the output devices of system 112 connected to computing device 204. The determination at block 515 can take a variety of forms. For example, computing device 204 can be configured simply to detect whether one or more of the instruments identified at block 510 is moving, based on image data continually received from tracking camera 224. If the instruments are stationary (or show movement below a predetermined threshold), the determination at block 515 is negative, and the performance of method 500 returns to block 510.

If, on the other hand, the instruments do show movement beyond zero, or beyond some other predetermined lower bound, the determination at block 515 is affirmative, and the performance of method 500 proceeds to block 520, to be discussed below. Alternatively, the determination at block 515 can be affirmative (that is, the input mode is active) if an instrument remains stationary and within a certain set distance of another instrument for a set amount of time.

In other embodiments, the determination by computing device 204 at block 515 can take other forms. For example, at block 515 computing device 204 may be configured to await specific input data, such as audible command (such as a voice command, e.g. "input on") recorded by microphone 420. In another example, computing device 204 may be configured to await a specific input from keyboard or mouse 416, or from another input device such as a foot pedal (not shown) available to surgeon 104.

Having determined that an input mode has been activated, at block 520 computing device 204 is configured to determine whether the tracked movements of the instruments identified at block 510 match any of the gesture definitions in repository 440. As will now be apparent to those skilled in the art, processor 400 continually receives image data (or instrument identifiers and positions, as mentioned above) from tracking camera 224 and processes such data according to conventional motion-tracking mechanisms to generate motion data (e.g. speed, direction, coordinates) for the instruments substantially in real-time. Processor 400 is therefore configured to compare the motion data to the definitions in repository 440, and determine whether the motion data matches any of the definitions.

Figure 8:
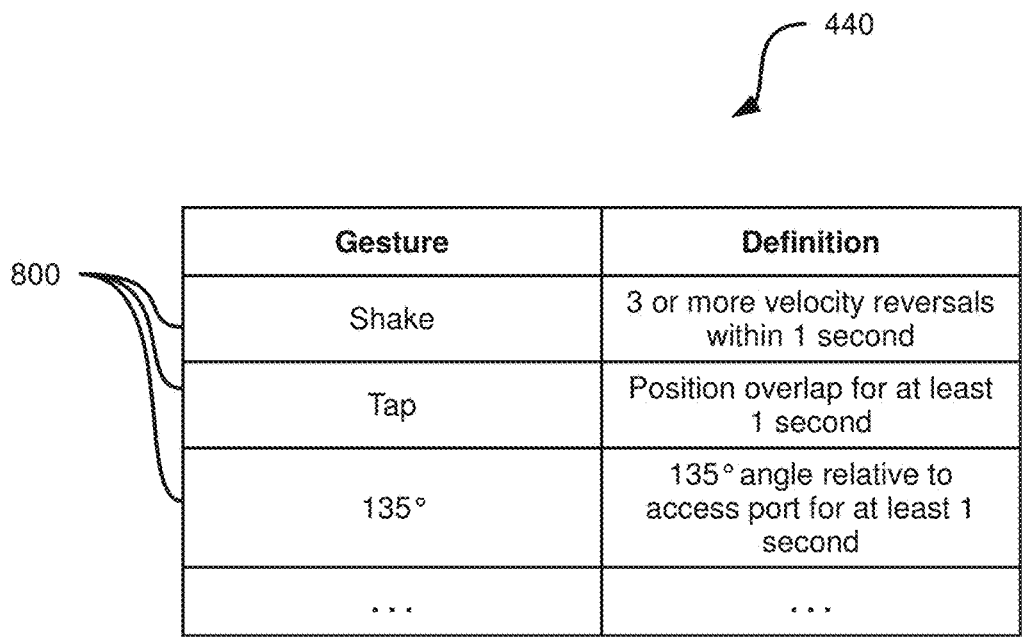
FIG. 8 depicts gesture definitions stored by the computing device of FIG. 4, according to a non-limiting embodiment.

Turning to FIG. 8, an example of gesture definitions repository 440 is shown. Repository 440 includes a plurality of records 800, each defining a gesture. Each record 800 includes a gesture identifier, and corresponding characteristics of that gesture. For example, a "shake" gesture is defined in the present example as three reversals in movement velocity of an instrument within a time period of one second, and a "tap" gesture is defined as a minimum of one second of overlap between the positions of two instruments, as determined by processor 400. A "135 degree" gesture is defined as an instrument being held at an angle of one hundred and thirty five degrees relative to the center of the access port. A wide variety of other gestures can also be defined, and other characteristics can be used to define such gestures. For example, certain gestures can be defined by the relative position of an instrument in comparison to segments of the field of view of scope 220, such that the presence of an instrument in a certain quadrant of the field of view for a certain time period is interpreted as a gesture by computing device 204. Other gestures can be defined by the speed or timing of a rotation of the instrument, the distance between the tips of two instruments, and the like.

Each record 800 can also specify tolerances (not shown) for the characteristics. For example, the time periods shown in FIG. 8 may have tolerances of 10%, such that three velocity reversals occurring in 1.1 seconds would still be interpreted as a "shake". Such tolerances, and any other gesture characteristics, can also be defined in association with a specific surgeon or surgical procedure. For example, a first surgeon may require gesture definitions with greater tolerances than a second surgeon.

Returning to FIG. 5, if the determination at block 520 is negative (that is, the motion data representing the movement of the identified instruments does not match any predefined gestures), the performance of method 500 returns to block 515. In other words, computing device 204 is configured to confirm whether or not an input mode remains active, and to monitor for any further movements that may match defined gestures.

If, on the other hand, the determination at block 520 is affirmative (that is, the movement of the identified instruments does match a predefined gesture), the performance of method 500 proceeds to block 525.

Figure 9:
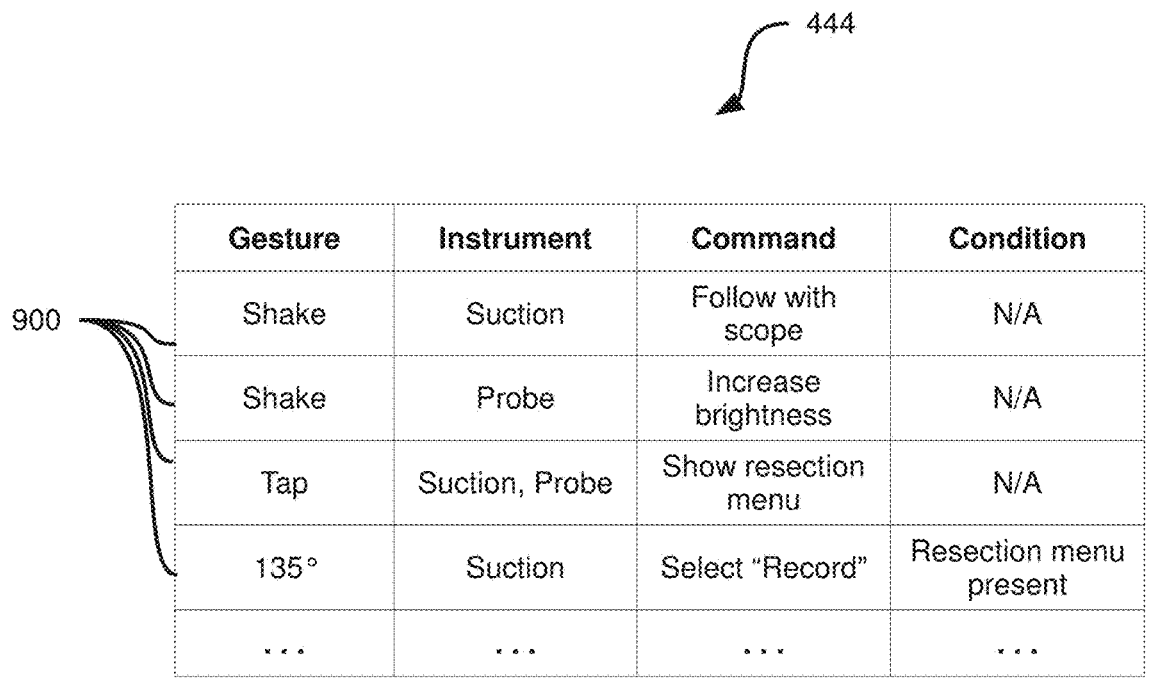
FIG. 9 depicts output control rule definitions stored by the computing device of FIG. 4, according to a non-limiting embodiment.

At block 525, computing device 204 is configured to select a command corresponding to the gesture detected at block 520, based on output control rules 444. Turning to FIG. 9, an example of rules 444 is shown. Rules 444 include a plurality of records 900 each defining an output control rule. Each record 900 includes a command definition for controlling one or more output devices of system 112. Each record 900 can also include, corresponding to the command definition, a gesture identifier and an instrument identifier.

In the present example, three rules are defined in rules 444. The first of records 900 defines a command that will cause robotic arm 216 to follow the motion of the suction instrument for a certain time after the suction instrument has registered a "shake" gesture. Such a command can be used to reposition scope 220. The second of records 900 defines a command that will cause an overhead light 424 to increase in brightness when a probe instrument registers a "shake" gesture. The third of records 900 defines a command that will cause display 208 to be updated to present a menu containing selectable interface elements relevant to tumor resection when the suction and probe instruments register a "tap" gesture. The fourth of records 900 defines a command that will cause a particular selectable element of the resection menu to be selected when the suction device is held at an angle of one hundred thirty five degrees in relation to the center of access port 228.

It will be understood that the rules shown in FIG. 9 are merely examples, and that a wide variety of other rules are also contemplated. As mentioned earlier, application 428 can contain a plurality of menus, each including various selectable elements. Rules 444 can contain one or more records defining conditions under which each of the plurality of menus is to be selected for presentation on display 208.

In some embodiments, additional parameters corresponding to the command definition can be included in a record 900, while in other embodiments some parameters can be omitted. Examples of other parameters include a stage of the surgical procedure (as defined in patient data 432); an identifier of a surgeon; characteristics of the image currently shown on display 208 (for example, image characteristics indicative of tumor tissue, such as brightness, contrast, or colour values); and other output data already provided to the output devices, such as which menu is currently presented on display 208. In general, rules 444 define associations between the context in which surgical instruments are being used, and commands to control the output devices of system 112.

Thus, at block 525 computing device 204 is configured to compare the identities of the instruments identified at block 510, the context of use of those instruments (e.g. gestures detected at block 520, stage of the procedure, identity of the surgeon), to rules 444 and select a rule that matches the current context. The command of that particular rule is the command selected at block 525.

Having selected a command at block 525, at block 530 computing device 204 is configured to update the control of the output devices of system 112 based on the selected command. The nature of the control effected at block 530 is defined by the particular command selected at block 525, and can therefore vary greatly. An example of a performance of block 530 is shown in FIG. 10.

Figure 10:
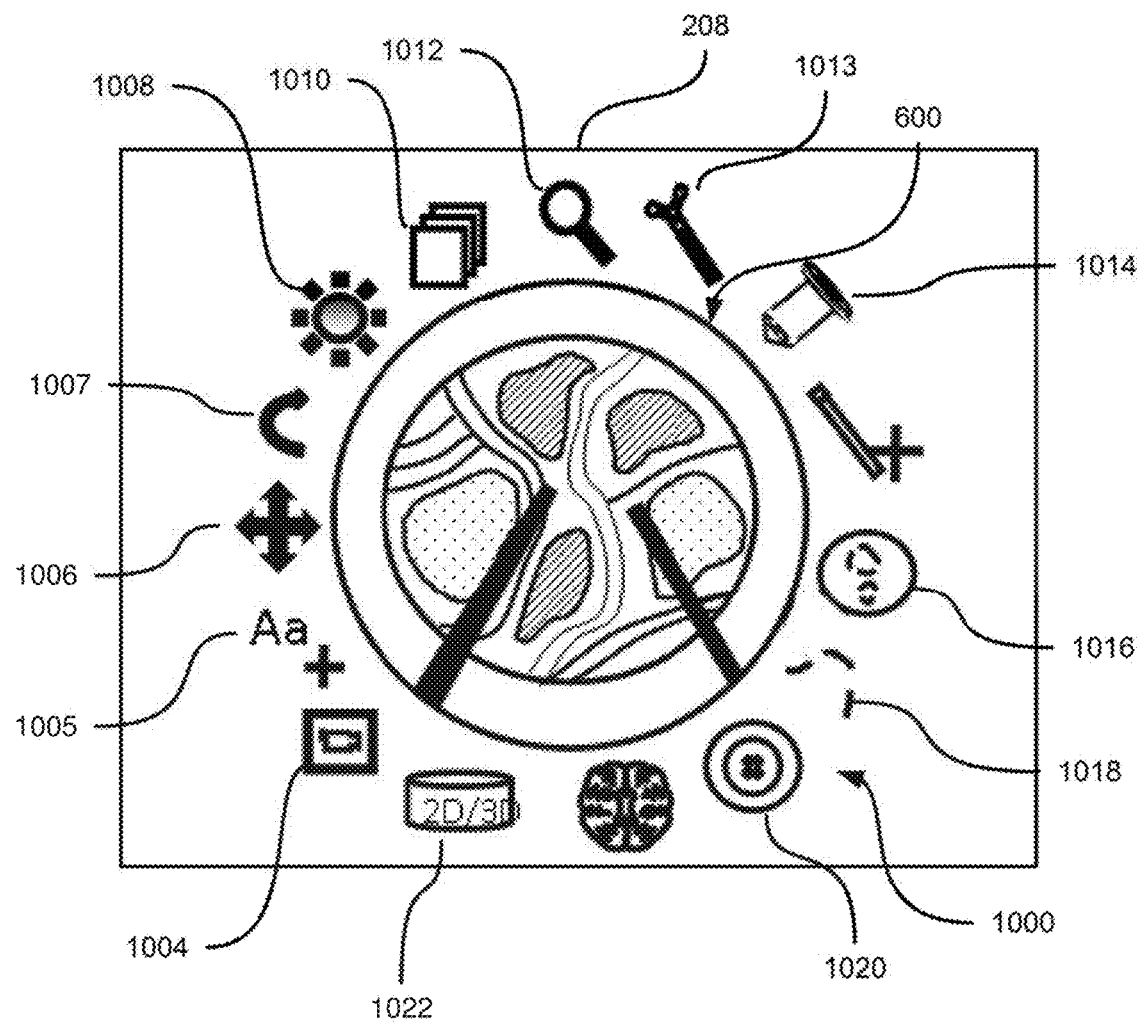
FIG. 10 depicts an example performance of block 530 of the method of FIG. 5, according to a non-limiting embodiment.

FIG. 10 depicts an updated interface presented on display 208, in which image 600 is shown following a "tap" gesture with the suction and probe instruments. In addition to image 600, which represents a frame of the video feed from scope 220 as discussed earlier, a menu 1000 is presented on display 208. Menu 100 is one of the plurality of menus within application 428, and includes a plurality of selectable elements. Each element is selectable for causing computing device 204 to execute a specific operation implemented by the instructions of application 428. For example, a record element 1004 causes computing device 204 to begin (or cease, if recording is already underway) storing the feed shown on display 208 in memory 404 as a video file. An annotation element 1005 allows text input for annotating image 600. A panning element 1006 allows image 600 to be panned in a plane parallel to the page of FIG. 10. A reset element 1007 resets the view shown on display 208 to a previous state (for example, before a recent panning operation). A brightness element 1008 causes computing device to present a further one of the plurality of menus within application 428 on display 208 for adjusting the brightness of display 208. Also included are a stack element 1010 and a magnification element, which 1012 causes computing device to present a still further one of the plurality of menus within application 428 on display 208 for adjusting the magnification of the video feed from scope 220.

Other examples of selectable elements include a tool selection element for selecting one of a plurality of tools identified by computing device 204. Such a selection may be used to restrict output control to the movements of a particular tool, for example. A port visibility element 1014 allows a rendering of access port 208 on display 208 to be toggled on and off (this functionality may also be extended to other tools). A region of interest element 1016 causes computing device 204 to begin tracking the movement of a given surgical instrument to draw a region of interest on image 600. A tract visibility element 1018 turns the presentation of fluid flow tracts (e.g. nerve fibre tracts, vasculature, and the like) on display 208 on and off. In addition, a skull stripping toggle element 1020 and a 2D/3D mode toggle element 1022 can be provided.

With menu 1000 presented on display 208, computing device 204 is configured to return to block 510 and continue monitoring the movements of any active instruments. Assuming that the instruments detected in the previous iteration of method 500 have not been removed from the field of view of tracking camera 224, the performance of blocks 510, 513 (optionally) and 515 will not effect any changes, and the performance of block 520 will determine whether any further input gestures have been made. Such input gestures may include a selection of an element of menu 1000 (for example, as specified in the fourth record 900 of FIG. 9), In response to selection of a menu element, computing device 204 is configured to generate further updated output data to enable the function corresponding to the selected element. As will now be apparent to those skilled in the art, numerous iterations of method 500 can be performed to control system 112, while reducing or avoiding the need for surgeon 104 to abandon the surgical instruments in favour of more conventional input devices (such as keyboard and mouse 416).

Figure 11:
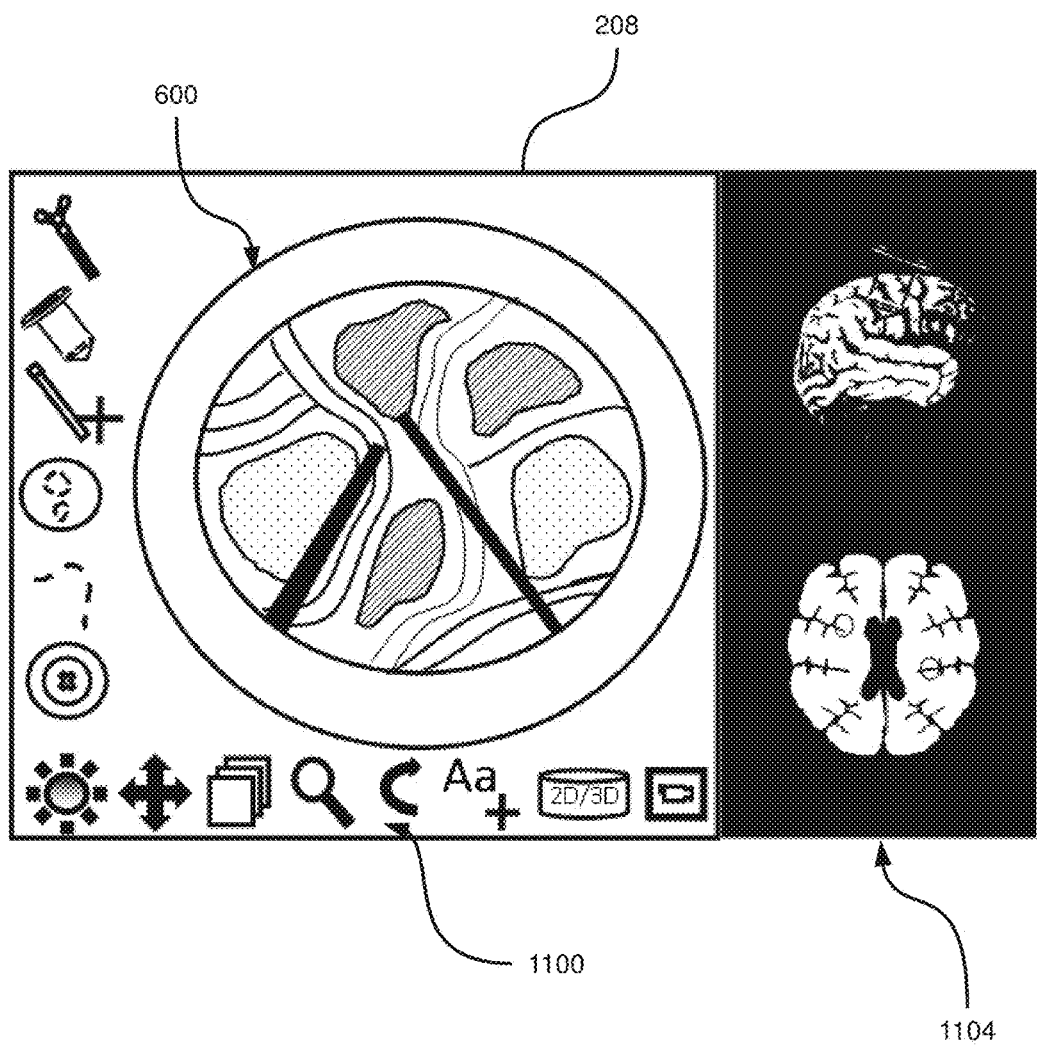
FIG. 11 depicts another example performance of block 530 of the method of FIG. 5, according to a non-limiting embodiment.
Figure 12:
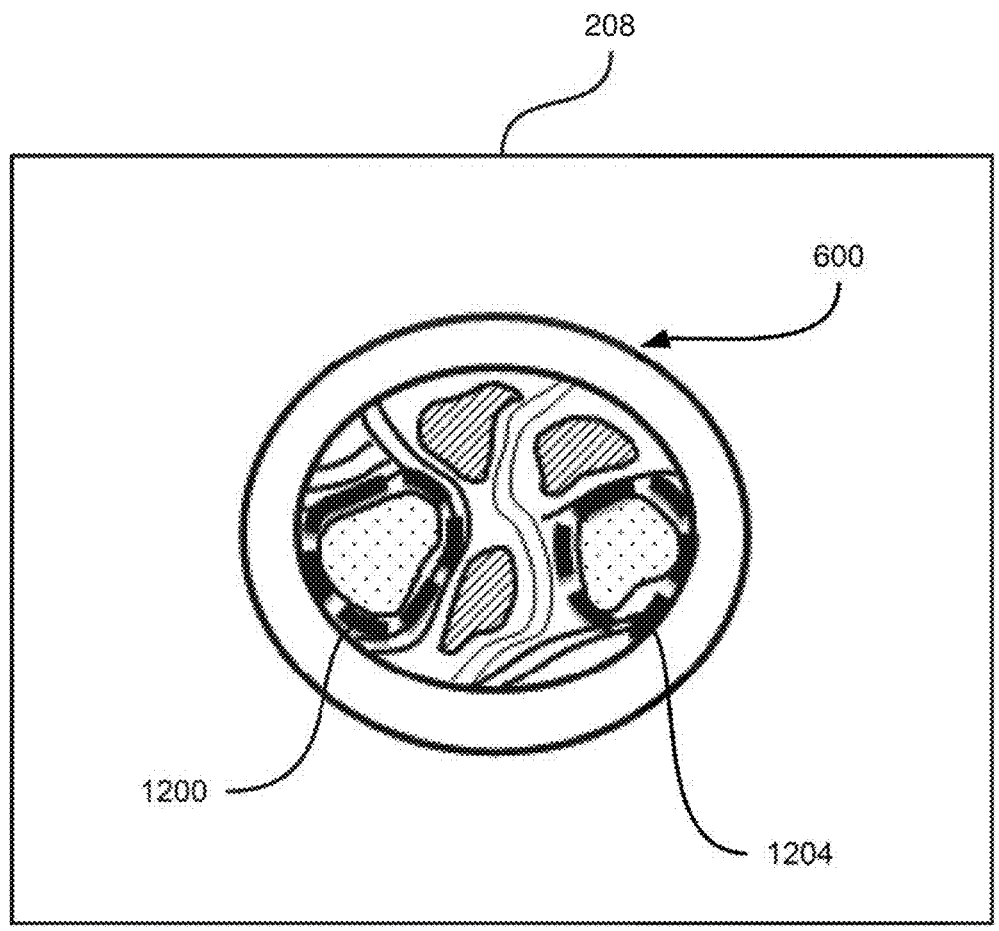
FIG. 12 depicts a further example performance of block 530 of the method of FIG. 5, according to a non-limiting embodiment.

FIGS. 11 and 12 provide further examples of output device control during the performance of method 500. FIG. 11 depicts display 208 presenting a menu 1100 (containing the same selectable elements as menu 1000, although in a different orientation), and image data 1104 retrieved from repository 432, in addition to image 600 as discussed above. FIG. 12 depicts image 600 on display 208. Menus 1000 and 1100 are no longer presented in FIG. 12 (they may be dismissed by certain instrument gestures, or by the selection of certain elements of menus 1000 or 1100. However, two regions of interest 1200 and 1204 are highlighted within image 600 on display 208. Regions of interest 1200 and 1204 are the result of further performances of method 500, in which a region of interest element such as element 1016 was selected, and further instrument gestures were detected to draw the regions. Computing device 204 can be configured to take various actions in connection with regions of interest 1200 and 1204. For example computing device 204 can apply a mask to image 600 to hide all of image 600 with the exception of regions 1200 and 1204.

Still other examples of output device control achieved through the performance of method 500 will occur to those skilled in the art. For example, images can be projected onto the patient's skull, and optical properties (e.g. magnification, focus and the like) of scope 220 can be altered. Further, individual selectable elements within the menus discussed above can be presented on display 208 in various orders and combinations.

A further example of output device control, particularly (although not exclusively) at block 513, involves masking out one or more portions of the surgical instruments identified at block 510. For example, scope 220 may have a shallow depth of field, and thus portions of the instruments that extend out of access port 228 towards scope 220 may appear out of focus on display 208. Computing device 204 can be configured, following the identification of the instruments, to generate output data including a mask of the identified instruments that can be combined with the video feed from scope 220 to obscure the unfocussed portions of the instruments with in-focus images of the instruments.

Figure 13:
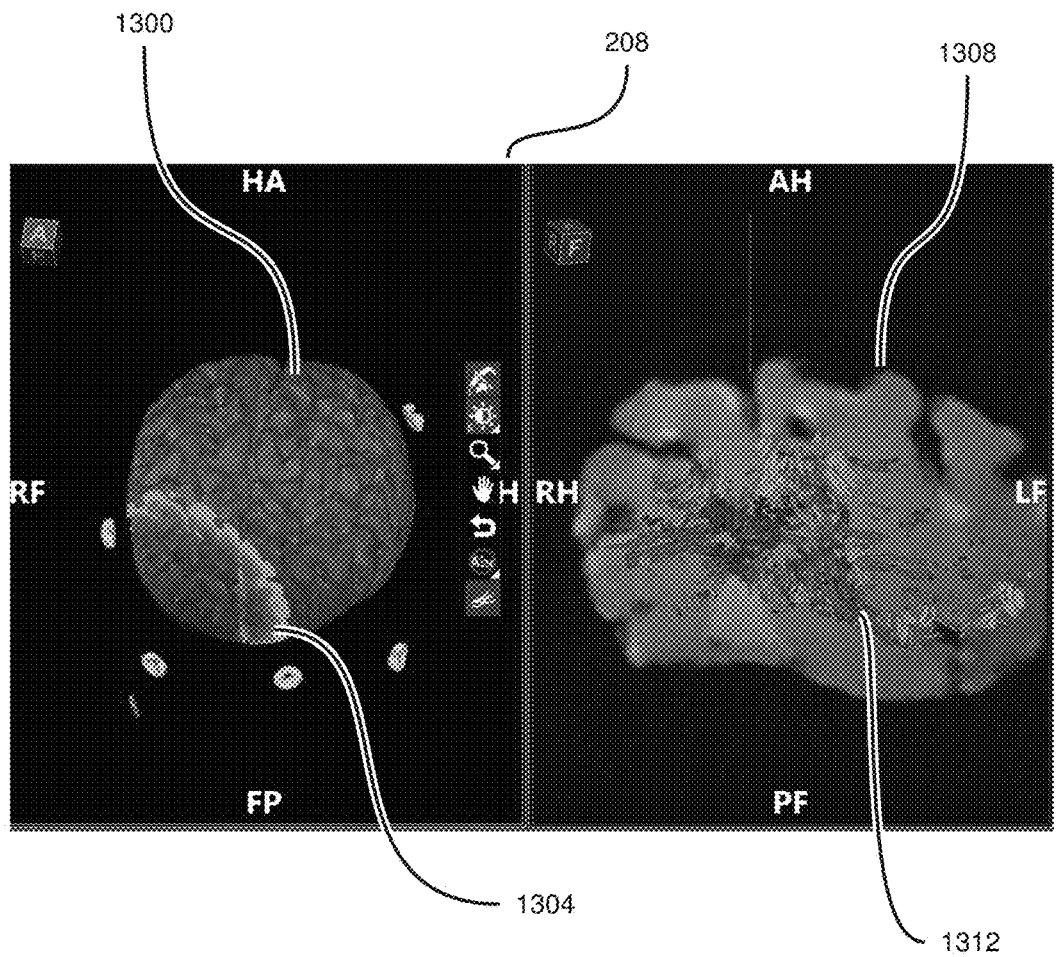
FIG. 13 depicts a further example performance of block 530 of the method of FIG. 5, according to a non-limiting embodiment.

Another example of output device control, referring now to FIG. 13, includes activating a display mode at block 530 referred to as radial stacking. In this display mode, computing device 204 is configured to present a three dimensional rendering 1300 of the brain in which a slice 1304 of brain tissue may be selected. Computing device 204 is configured to determine the location and plane of slice 1304 based on, for example, instrument movements matched with known gestures at block 520. Computing device 204 can also be configured to control display 208 to present a two dimensional cross-section 1308 of three dimensional model 1300, taken in the plane of slice 1304. A variety of display layers can be presented on cross section 1308, again based on further motions of surgical instruments detected by computing device 204. In the present example, fluid flow tracts 1312 are presented on cross section 1308 (for example, in response to a selection of a menu element such as element 1018).

Figure 14:
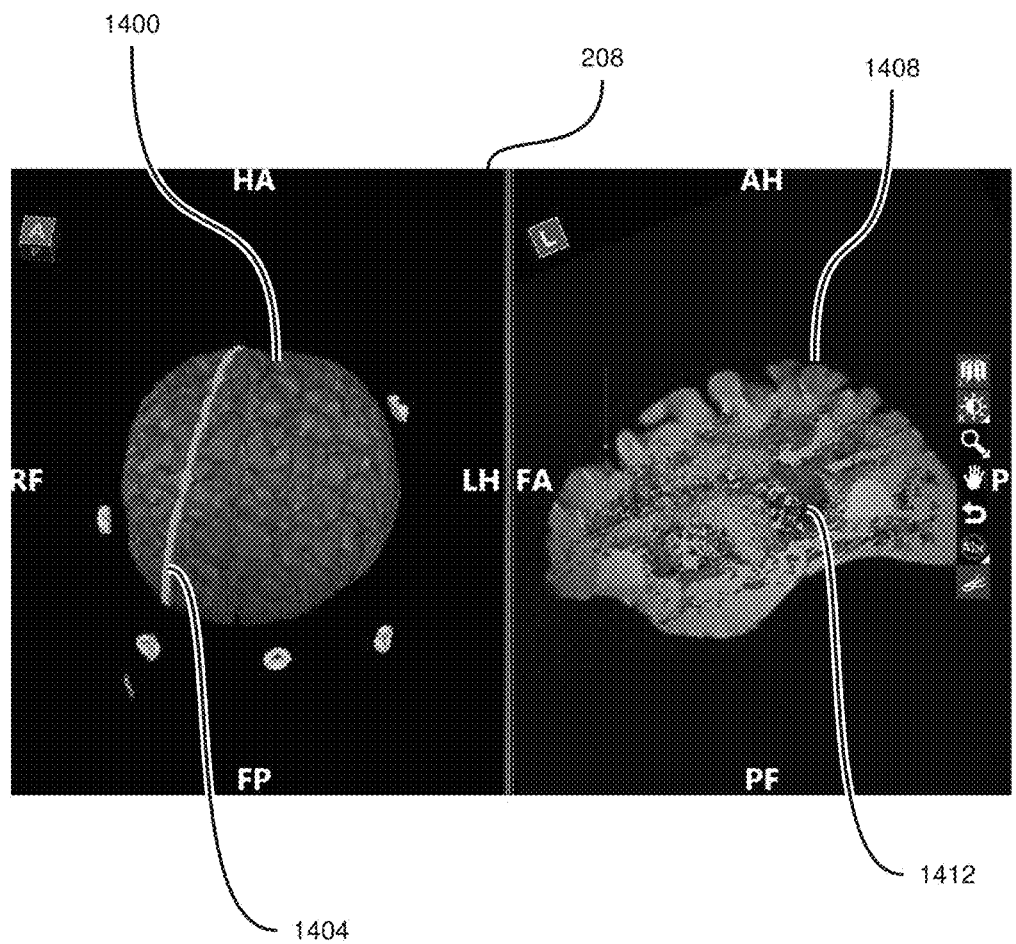
FIG. 14 depicts a further example performance of block 530 of the method of FIG. 5, according to a non-limiting embodiment.

Computing device 204 can also be configured to control display 208 to update the position of slice 1304, and the appearance of cross section 1308, based on further movement of surgical instruments. Turning to FIG. 14, an updated rendering 1400 is shown, in which an updated slice 1404 is depicted. Slice 1404 may be a rotated version of slice 1304, the rotation of which can be controlled by movement of surgical instruments. Similarly, a cross section 1408 is also presented on display 208, representing an updated version of cross section 1308 resulting from the new position of slice 1404. Tracts 1412 are also updated in cross section 1408. It will now be apparent that through manipulation of surgical instruments, it is possible to cause slice 1304 to sweep through a full 360° rotation, or to relocate to any location or angle within the brain. In some embodiments, displayed elements such as tracts 1312 and 1412 may also be restricted to only certain areas of the current slice, such as an area within the current slice and also within a predetermined distance of a tool tip (detected at block 520). Elements such as tracts 1312 and 1412 in cross sections 1308 and 1408 can also have configurable depths; that is, tracts 1312 and 1412 can be displayed not only for the exact plane of slices 1304 and 1404, but also for a configurable number of adjacent planes parallel to those planes.

In still further embodiments, movements of surgical instruments detected by computing device 204 can be used to present three dimensional renderings of those instruments on display 208, in addition to or instead of a video feed from scope 220. For example, a model such as rendering 1300 can be updated to show the position of surgical instruments, including access port 228, tracking their movements substantially in real time. Additional information can also be presented on such renderings.

Figure 15A:
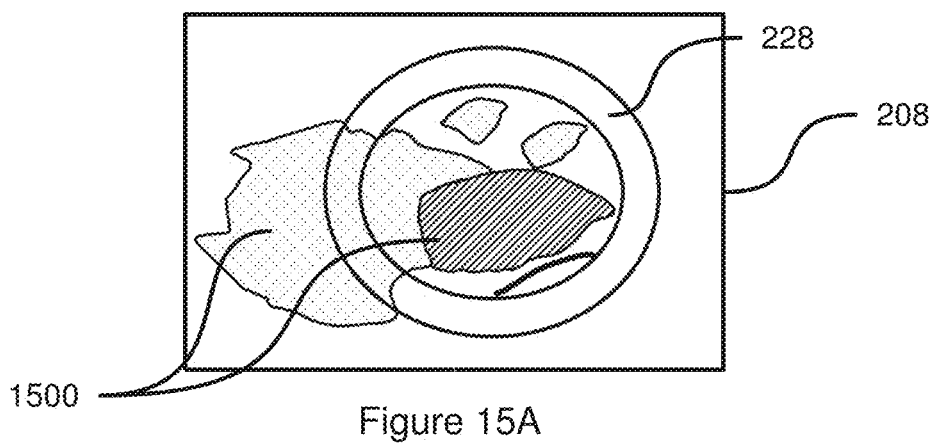
FIGS. 15A, 15B and 15C depict further example performances of block 530 of the method of FIG. 5, according to a non-limiting embodiment.
Figure 15B:
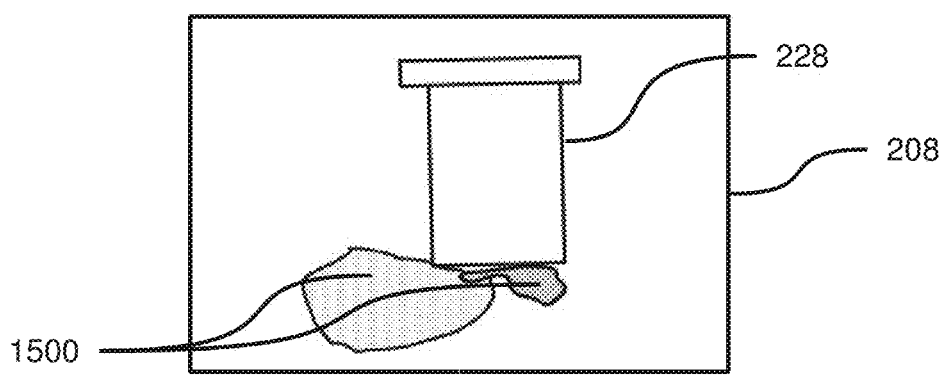
Figure 15C:
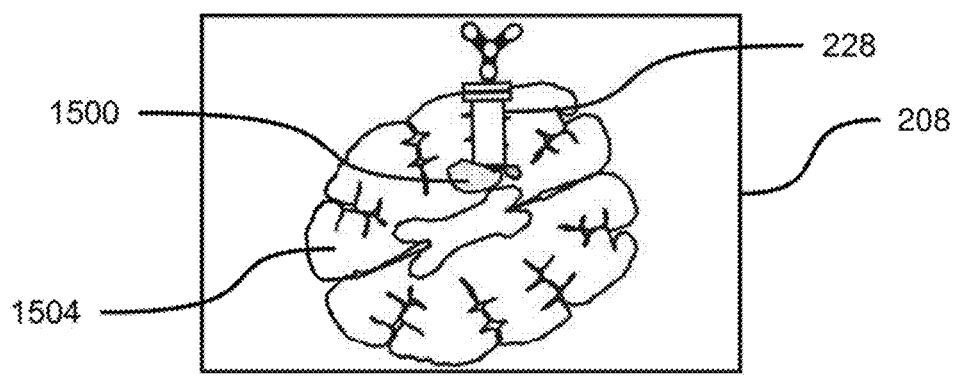

For example, a rendering of a tumor whose location and size are stored in repository 432 can be presented on display 208. In some examples, a rendering of a tumor or other data from repository 432 can be overlaid on a video feed (that is, a non-virtual feed) from scope 220. The rendering can be located and scaled on display 208 (for example, on image 600 discussed above) based on the current magnification of scope 220 and the location of access port 228. Referring to FIGS. 15A, 15B and 15C, examples of output data presented on display 208 in this embodiment are shown. FIG. 15a shows a modified version of the display shown in FIG. 6, in which a video feed from scope 220 showing access port 228 is supplemented with a (virtual) rendering of a tumour 1500 in two or three dimensions, indicating that the tumour is larger than the field of view into the patient's brain afforded by access port 228.

FIG. 15B shows a rendering of access port 228 and tumour 1500 in an orientation perpendicular to the axis of access port 228. The display of FIG. 15B is generally virtual rather than being supplemented with video from scope 220.

FIG. 15C shows an additional rendering of tumour 1500, the patient's brain 1504, and access port 228, depicting the scale of access port 228 relative to the entire brain 1504 and tumour 1500. The views of FIGS. 15A-15C can be controlled through method 500, and can also be combined on display 208 (for example, in three panes).

Variations to the above systems and methods are contemplated. For example, in some embodiments equipment tower 200 can be omitted entirely or replaced with two or more towers. Additionally, in some embodiments computing device 204 need not be co-located with the remainder of system 112. Instead, computing device 204 can be connected to the remainder of system 112 via a network, such as the Internet. In still other variations, computing device 204 can be implemented in a distributed computing framework.

In still further variations, markers and tracking technologies other than IR can be employed. For example, markers 236 can include RFID tags, electromagnetic sensors, LEDs or the like. In still other variations, markers 236 can be omitted entirely, and computing device 204 can instead be configured to employ known image processing techniques to locate and identify surgical instruments in the field of view of tracking camera 224 or any other suitable tracking system.

A portion of the disclosure of this patent document contains material which is subject to copyright protection. The copyright owner has no objection to the facsimile reproduction by any one the patent document or patent disclosure, as it appears in the Patent and Trademark Office patent file or records, but otherwise reserves all copyrights whatsoever.

Persons skilled in the art will appreciate that there are yet more alternative implementations and modifications possible for implementing the embodiments, and that the above implementations and examples are only illustrations of one or more embodiments. The scope of the claims should not be limited by the embodiments set forth above, but should be given the broadest interpretation consistent with the description as a whole.

We claim:

1. A method of controlling a surgical navigation system, comprising:
   storing, in a non-transitory memory, (i) a plurality of gesture definitions each defining one of a plurality of distinct predetermined sequences of movements of a surgical instrument, (ii) for each gesture definition, a corresponding identifier of one of a plurality of commands, and (iii) for each command, a corresponding condition under which the command is to be executed;
   receiving, at an input device distinct from the surgical instrument, an input signal;
   responsive to receiving the input signal, determining, at a processor connected to the memory, whether to activate an input mode;

responsive to activating the input mode, obtaining, at the processor, motion data representing movement of the surgical instrument over a configurable period of time set by the gesture definitions, based on positions of the surgical instrument received from a tracking system having a field of view encompassing the surgical instrument;

comparing the motion data to the plurality of gesture definitions;

when the motion data matches one of the gesture definitions, retrieving the command identifier corresponding to the one of the gesture definitions;

evaluating the condition corresponding to the command identified by the retrieved command identifier;

when the condition is satisfied, executing, at the processor, the command identified by the retrieved identifier to generate output data; and transmitting the output data to a device connected to the processor, for controlling the device.

2. The method of claim 1, further comprising:
receiving image data at the processor from the tracking system;
receiving the positions by storing a surgical instrument definition and determining the positions by comparing the image data with the surgical instrument definition.

3. The method of claim 1, further comprising:
storing a plurality of selectable interface elements;
wherein generating the output data comprises retrieving a subset of the selectable interface elements; and
wherein transmitting the output data comprises presenting the subset on a display.

4. The method of claim 1, further comprising:
presenting a plurality of selectable interface elements on a display;
wherein generating the output data comprises selecting one of the selectable interface elements presented on the display.

5. The method of claim 1, wherein transmitting the output data comprises transmitting respective portions of the output data to at least one of a display, a projector, and a robotic arm.

6. The method of claim 1, further comprising: receiving an identifier of the surgical instrument at the processor from the tracking system with the positions.

7. The method of claim 1, wherein the device comprises a display, and wherein transmitting the output data comprises controlling the display to present a rotatable slice in a three dimensional model of brain tissue.

8. The method of claim 7, wherein transmitting the output data further comprises controlling the display to rotate the slice about an axis based on the identifier of the surgical instrument.

9. The method of claim 1, wherein the device comprises a display; the method further comprising:
storing a tumour definition in the memory;
transmitting the output data by controlling the display to present a model of the tumour in conjunction with one of a video feed of an access port instrument, and a model of the access port instrument.

10. A computing device, comprising:
a non-transitory memory storing (i) a plurality of gesture definitions each defining one of a plurality of distinct predetermined sequences of movements of a surgical instrument, (ii) for each gesture definition, a corresponding identifier of one of a plurality of commands, and (iii) for each command, a corresponding condition under which the command is to be executed;
a processor connected to the memory;
an interface connecting the processor to a tracking system; and
a device connected to the processor;
the processor configured to:
receive, at an input device distinct from the surgical instrument, an input signal;
responsive to receiving the input signal, determine, at a processor connected to the memory, whether to activate an input mode;
responsive to activating the input mode, obtain motion data representing movement of the surgical instrument over a configurable period of time set by the gesture definitions, based on positions of the surgical instrument received from a tracking system having a field of view encompassing the surgical instrument;
compare the motion data to the plurality of gesture definitions;
when the motion data matches one of the gesture definitions, retrieve the command identifier corresponding to the one of the gesture definitions;
evaluate the condition corresponding to the command identified by the retrieved command identifier;
when the condition is satisfied, execute the command identified by the retrieved identifier to generate output data; and
transmit the output data to the device for controlling the device.

11. The computing device of claim 10, wherein the memory stores store a surgical instrument definition, and wherein the processor is further configured to:
receive image data from the tracking system; and
determine the positions by comparing the image data with the surgical instrument definition.

12. The computing device of claim 10, wherein the memory stores a plurality of selectable interface elements; wherein the output device includes a display, and wherein the processor is further configured to:
generate the output data by retrieving a subset of the selectable interface elements from the memory; and
transmit the output data by presenting the subset on the display.

13. The computing device of claim 10, the processor further configured to:
present a plurality of selectable interface elements on a display;
generate the output data by selecting one of the selectable interface elements presented on the display.

14. The computing device of claim 10, wherein the device includes one or more of a display, a projector and a robotic arm; the processor further configured to transmit the output data by transmitting respective portions of the output data to at least one of the display, the projector, and the robotic arm.

15. The computing device of claim 10, the processor further configured to receive an identifier of the surgical instrument from the tracking system with the positions.

16. The computing device of claim 10, wherein the device comprises a display, the processor further configured to transmit the output data by controlling the display to present a rotatable slice in a three dimensional model of brain tissue.

17. The computing device of claim 16, the processor further configured to transmit the output data further by controlling the display to rotate the slice about an axis based on the identifier of the surgical instrument.

18. The computing device of claim 10, wherein the memory stores a tumour definition, and wherein the device comprises a display; the processor further configured to transmit the output data by controlling the display to present a model of the tumour in conjunction with one of a video feed of an access port instrument, and a model of the access port instrument.

19. A non-transitory computer-readable medium storing a plurality of computer readable instructions executable by a processor for implementing a method comprising:

storing; in a non-transitory memory connected to the processor, (i) a plurality of gesture definitions each defining one of a plurality of distinct predetermined sequences of movements of a surgical instrument, (ii) for each gesture definition, a corresponding identifier of one of a plurality of commands, and (iii) for each command, a corresponding condition under which the command is to be executed;

receiving, at an input device distinct from the surgical instrument, an input signal;

responsive to receiving the input signal, determining, at a processor connected to the memory, whether to activate an input mode;

responsive to activating the input mode; obtaining, at the processor, motion data representing movement of the surgical instrument over a configurable period of time set by the gesture definitions, based on positions of the surgical instrument received from a tracking system having a field of view encompassing the surgical instrument;

comparing the motion data to the plurality of gesture definitions;

when the motion data matches one of the gesture definitions, retrieving the command identifier corresponding to the one of the gesture definitions;

evaluating the condition corresponding to the command identified by the retrieved command identifier;

when the condition is satisfied, executing, at the processor, the command identified by the retrieved identifier to generate output data; and transmitting the output data to a device connected to the processor, for controlling the device.

* * * * *